United States Patent [19]

Fryslie

[11] Patent Number: 4,667,666
[45] Date of Patent: May 26, 1987

[54] PROTECTIVE BANDAGING DEVICE

[76] Inventor: Alice Fryslie, 17133 E. Salida Dr., Fountain Hills, Ariz. 85268

[21] Appl. No.: 853,655

[22] Filed: Apr. 18, 1986

[51] Int. Cl.⁴ .............................................. A61L 15/00
[52] U.S. Cl. ................................................... 128/156
[58] Field of Search ............................... 128/156, 154

[56] References Cited

U.S. PATENT DOCUMENTS

| | | | |
|---|---|---|---|
| 2,785,677 | 3/1957 | Stumpf | 128/156 |
| 3,245,855 | 4/1966 | Stenvall | 128/156 |
| 4,212,296 | 7/1980 | Schaar | 128/156 |

Primary Examiner—Gregory F. McNeill
Attorney, Agent, or Firm—Richard R. Mybeck

[57] ABSTRACT

A protective bandaging device having a foraminous flat or domed shaped upper surface supported by relatively rigid impervious side walls depending downwardly therefrom to an outreaching flange having a layer of a suitable medical grade adhesive disposed upon the lower surface thereof which, upon removal of a shaped conforming release paper therefrom is securable to the human body in circumscription about the wound, cut, abrasion or incision whose protection during the healing cycle is desired.

12 Claims, 4 Drawing Figures

U.S. Patent   May 26, 1987   4,667,666
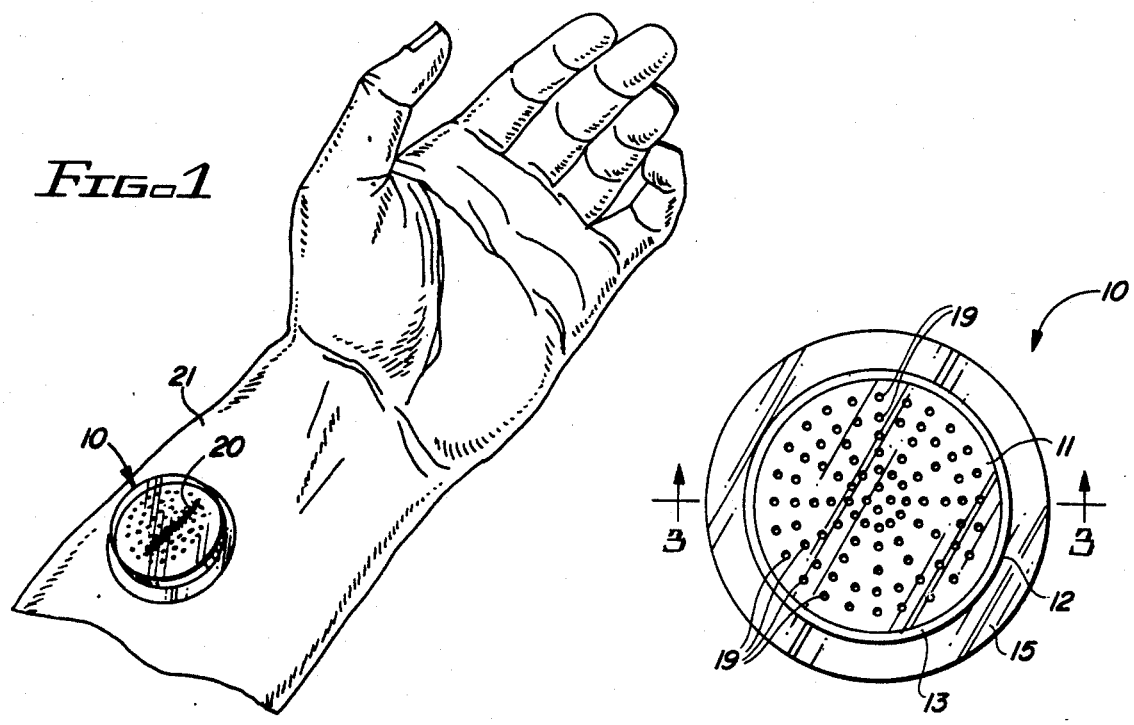
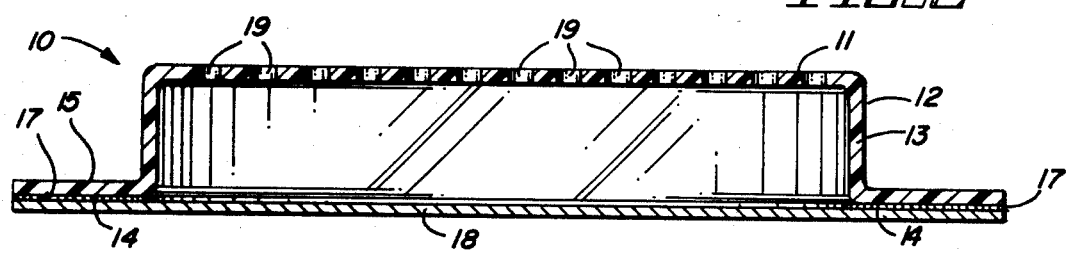
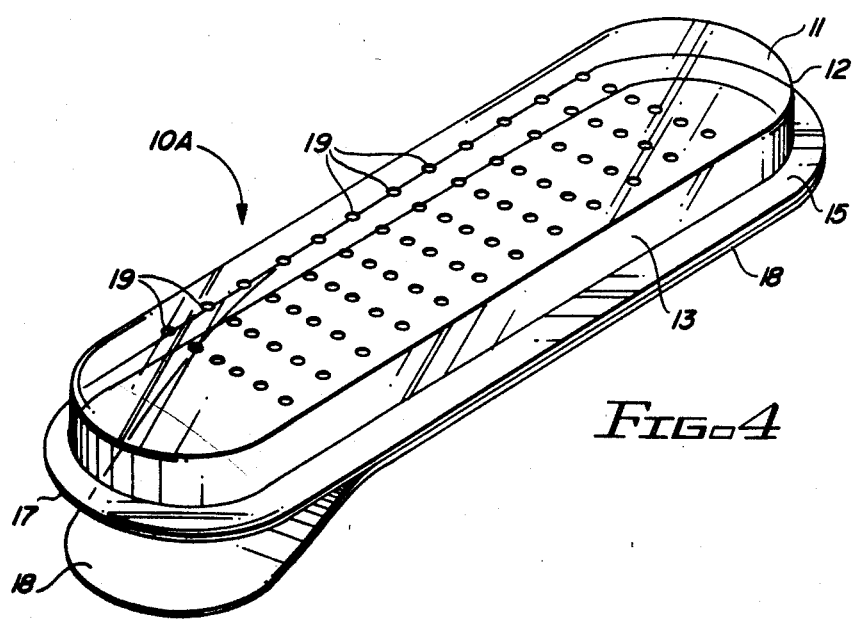

PROTECTIVE BANDAGING DEVICE

INTRODUCTION

The present invention relates to protective bandaging and more particularly to a disposable protective device for use to cover wounds, cuts, abrasions, or incisions and the like (herein collectively referred to as "wounds") during their healing process which is capable of responding to normal body movements without detachment or fracture and which provides a ventilated healing chamber without actually engaging the area to be healed.

BACKGROUND OF INVENTION

The art through the years has endeavored to provide protective devices for wounds, cuts, incisions and abrasions to enhance the healing process while attempting to shield the injured tissue from unwanted or unexpected bumps and abrasions which dislodge the scab formation and from foreign matter which would otherwise impede the natural progress of the healing.

One of the more popular of such devices was the so-called BAND-AID ® which was developed and marketed by Johnson and Johnson of Rahway, N.J. This device comprises a gauze-like pad, with or without antiseptic impregnated therewithin, which engages the wound, and a pair of adhesive tape strips, each extending away from the pad, to secure the bandage to the skin adjacent the wound. While serving a need in the health care field, such bandages also suffered from the propensity of the scab to "grow" into the gauze-like pad with the end result that in changing a soiled pad, the scab was also frequently removed prematurely with the result that the healing process was substantially retarded. A further disadvantage of the BAND-AID ® device resulted when it was applied to especially hirsute individuals who found that their hairs which were disposed beneath the tape fasteners were literally torn out by their roots when the tapes were removed.

Through the succeeding years, variants were presented in an attempt to obviate these problems. Such variations including the use of dome or cup-shaped covers secured ty separate adhesive means as shown in Lesher, (U.S. Pat. No. 2,632,443), Schimmel, (U.S. Pat. No. 3,334,626) and Connally, (U.S. Pat. No. 1,616,156).

Other variations such as that described in Reinitz, (U.S. Pat. No. 1,956,695) involved transparent impermeable device secured by an adhesive strip for collecting secretions while Barbieri (U.S. Pat. No. 3,874,387) disclosed a similar device which included fluid valves. Stumpf, (U.S. Pat. No. 2,785,677) and Schaar, (U.S. Pat. No. 4,212,296) each disclose a protective device having a domed portion but each suffered from a "green house" effect whereby bacteria were "cultured" at the wound site and instead of healing, the wound became infected.

Further, none of these prior devices were able to provide the protected wound with the healing environment desired nor were they able to create the mechanically stable protection necessary to prevent premature dislodgement of the scab formation.

Accordingly, it is apparent that a major need remains unfilled in the care and protection of human wounds and like insults to human tissue and it is toward this need that the present invention is directed.

SUMMARY OF THE INVENTION

The present invention comprises a disposable protective device for use with wounds, cuts, or incisions and the like which device has a foraminous flat or dome-shaped upper surface supported by relatively rigid, impervious side walls depending downwardly therefrom generally normal from the perimeter thereof and terminating in a flexible outreaching flange upon which a layer of a suitable medical grade adhesive is disposed and covered by a complementary layer of release paper. Upon removal of the release paper from the surface of the adhesive layer, the device can be securely attached to the human body in circumscription about the wound, cut, and the like for which protection during the healing cycle is desired by pressing the adhesive layer into adherent engagement with the skin surrounding the wound.

Accordingly, it is a prime object of the present invention to provide a new and improved bandaging device for covering and protecting wounds, cuts, abrasions or incisions during the healing process which permits an adequate presence of ambient air while avoiding the deleterious effect of physical contact and "green house" effect.

Another object of the present invention is to provide a new and improved disposable protective device for wounds, cuts, abrasions, incisions and the like which device surrounds the damaged tissue without engaging it to provide a foraminous cover supported in substantially rigid spaced relationship to the wound to create a secure healing conducive environment throughout the healing process.

A further object of the present invention is to provide a new and improved protective bandaging device which is capable of remaining in position in protective circumscription about a wound whose healing is desired throughout the normal movement of the body portion to which it is secured.

These and still further objects as shall hereinafter appear are fulfilled by the present invention in a remarkably unexpected fashion as will be readily discerned from the following detailed description of exemplary embodiments thereof, especially when read in conjunction with the accompanying drawing in which like parts bear like numerals throughout the several views.

BRIEF DESCRIPTION OF DRAWINGS

In the drawings:

FIG. 1 is an isometric view of a human hand having a bandaging device embodying the present invention attached thereto;

FIG. 2 is a plan elevation of the device shown in FIG. 1;

FIG. 3 is a cross section taken on line 3—3 of FIG. 2; and

FIG. 4 is an isometric view of an alternate bandaging device embodying the present invention.

DESCRIPTION OF PREFERRED EMBODIMENTS

The present invention relates to a disposable protective bandaging device indicated at 10 and 10A, for use with cuts, wounds, and the like comprising a foraminous top portion 11 having a perimeter 12, an impervious, generally rigid side portion 13 integrally formed with said top portion 11 at the perimeter 12 thereof and depending therefrom to a lower edge 14. A relatively flexible outreaching flange portion 15 is integrally formed with side portion 13 at lower edge 14 and extends outwardly therefrom to define a bottom surface 16 upon which a layer of medical grade adhesive 17 is disposed in shaped conforming relationship thereto. A layer of release paper 18 is laid over and detachably secured to adhesive layer 17 in shape conforming protective relationship thereto. A circular embodiment is identified at 10 in FIGS. 1-3 whereas an oblong device has been designated 10A in FIG. 4. It is of course understood that other geometric shapes can be devised for this device within the scope of this teaching wherein a foraminous top, a substantially rigid impervious side wall and an adhesively coated flexible bottom flange are the essential elements for obtaining the unexpected benefits hereof.

Device 10 can be readily manufactured using conventional techniques such as injection molding or extrusion. Preferably, the device will be injection molded from readily available plastics such as, cellulose acetate butyrate ("CAB"); Nylon ® 6 (a polyamide available from DuPont); poly formaldehyde (available as DELRIN ® from DuPont); polyvinyl chloride ("PVC"); polyethylene terephthalate ("PET") (available as MYLAR ®) and the like. The primary consideration in selecting the material from which the device is formed is its physiological compatibility with human skin, its combination of sufficient rigidity for protection with sufficient flexibility to avoid detachment during ordinary human activity. Each of the above listed compositions are capable of meeting the standards indicated for them and have the further desirable characteristic of stability at their fusion point which permits fabrication by either injection molding or extrusion, as the exigencies of a particular configuration may dictate.

The medical grade adhesive employed herein may be any of the several such adhesives approved by the U.S. Food, Drug and Cosmetics Administration such as MED #3044 (Fasson) or its equivalent.

The protective release paper may be formed of glassine or other pretreated protective material characterized by its non-invasive adherence to the adhesive layer. It has been found preferable in most embodiments to score the release paper before covering the adhesive so that it can be readily removed without contaminating the adhesive layer.

It should be further noted that the combination of rigidity and flexibility described above is especially beneficial to the ultimate performance of the device in that the rigidity permits the device to protect the wound surface from unexpected and unwanted engagement by a foreign object while the flexibility of the device permits the device to move with the body portion as the body completes its normal mechanical movements without disengaging the device from its protective position around the wound. The foraminae 19 in top portion 11 can either be created during the forming process or drilled after the formed member is cooled.

To protectively cover a typical wound 20 disposed in a portion of the human body such as an arm 21, release paper 18 is peeled off of and removed from adhesive layer 17 thereby exposing the adhesive layer 17. Next, the device 10 is pressed onto the arm 21 adhesive layer 17 first and positioned in circumscription about the wound 20. When thus placed, device 10 protects wound 20 from extraneous insult by the coaction of flange 15 and impervious side portion 13 to maintain foraminous top surface 11 in spaced breathing relationship to wound 20. The healing process is further facilitated by the passage of air through the foraminae 19 into the wound containing chamber while preventing the creation of a "green house" effect which would otherwise facilitate the growth of deleterious cultures at the wound site and impede its normal healing process. Of course it is understood that reference to the arm 21 herein is for illustrative purposes only and that device 10 is equally well suited for application to the leg, torso, back, buttock, neck, face or any other location for which such protection is needed.

From the foregoing, it is readily apparent that protective bandaging devices have been herein described and illustrated which fulfill all of the aforestated objectives in a remarkably unexpected fashion. It is, of course, understood that such modification, alterations and adaptations, as may readily occur to the artisan skilled in the field to which this invention pertains when confronted with this specification, are intended within the spirit of the present invention which is limited only by the scope of the claims appended hereto.

Accordingly what is claimed is:

1. A bandaging device for protecting a wound, cut, abrasion, incision or the like during the healing process without creating physical contact therewith, said device comprising a foraminous top portion having a perimeter, an impervious side portion integrally formed with said perimeter and depending therefrom to a lower edge, an outreaching semi-rigid flexible flange portion integrally formed with said lower edge and extending outwardly therefrom defining a lower surface; a layer of medical grade adhesive disposed upon said lower surface in shaped conforming relationship thereto; and a layer of release paper detachably secured to said adhesive layer in shape conforming relationship thereto.

2. A devise according to claim 1 in which said top portion is flat.

3. A devise according to claim 1 in which said top portion is doomed.

4. A devise according to claim 2 in which said side portion is disposed in substantially normal relationship to said top portion.

5. A devise according to claim 3 in which said side portion is disposed in substantially normal relationship to said top portion.

6. A device according to claim 4 in which said lower surface is annular.

7. A device according to claim 5 in which said lower surface is annular.

8. A device according to claim 4 in which said lower surface is oblong.

9. A device according to claim 5 in which said lower surface is oblong.

10. A device according to claim 1 in which said top portion and said side portion cooperate to define a hemisphere.

11. A device according to claim 8 in which said lower surface is annular.

12. A method of providing non-engaging protection for a live tissue wound during its healing process with a device comprising a foraminous top portion having a perimeter, an impervious side portion integrally formed with said perimeter and depending therefrom to a lower edge, an outreaching flange portion integrally formed with said lower edge and extending outwardly therefrom to define a lower surface, a layer of medical grade adhesive disposed upon said lower surface in shape conforming relationship thereto, and a layer of release paper detachably secured to said adhesive layer in shape conforming relationship thereto, said method consisting of the steps of: removing the release paper from the medical grade adhesive; pressing the medical grade adhesive into adhering engagement with said live tissue in circumscription about the wound; and leaving said device in place until the healing of said wound is complete.

* * * * *